United States Patent [19]

Reed

[11] Patent Number: 4,951,668

[45] Date of Patent: Aug. 28, 1990

[54] ELECTRICAL IMPULSE APPARATUS

[76] Inventor: Don R. Reed, 316 Capitol, Fort Gibson, Okla. 74434

[21] Appl. No.: 381,316

[22] Filed: Jul. 18, 1989

[51] Int. Cl.⁵ ............................................. A61N 1/00
[52] U.S. Cl. ................... 128/419 R; 128/421
[58] Field of Search .............. 128/421, 422, 419 PG, 128/419 R, 419 S; 231/7

[56] References Cited

U.S. PATENT DOCUMENTS

| | | | |
|---|---|---|---|
| 2,920,193 | 6/1960 | Breckman | 128/421 |
| 3,635,224 | 2/1972 | Berkovits | 128/419 PG |
| 4,155,366 | 5/1979 | Di Mucci | 128/421 |

OTHER PUBLICATIONS

"Shocks for Snakebites", by Robert Herzberg, Jun. 87, Outdoor Life, pp. 55-57, 110-111.

Primary Examiner—Francis Jaworski
Assistant Examiner—George Manuel

[57] ABSTRACT

A field portable electrical impulse apparatus is disclosed for reducing the adverse affects on living tissue of pest attacks and poison injection. The apparatus includes a direct current electrical energy source connected by way of a rotary-type switch to a plurality of capacitors. The outputs of the capacitors are connected to a probe's electrodes so that various current levels can be selected. When the probe is placed into contact with the affected living tissue the desired level of electrical energy is applied directly thereto.

4 Claims, 1 Drawing Sheet

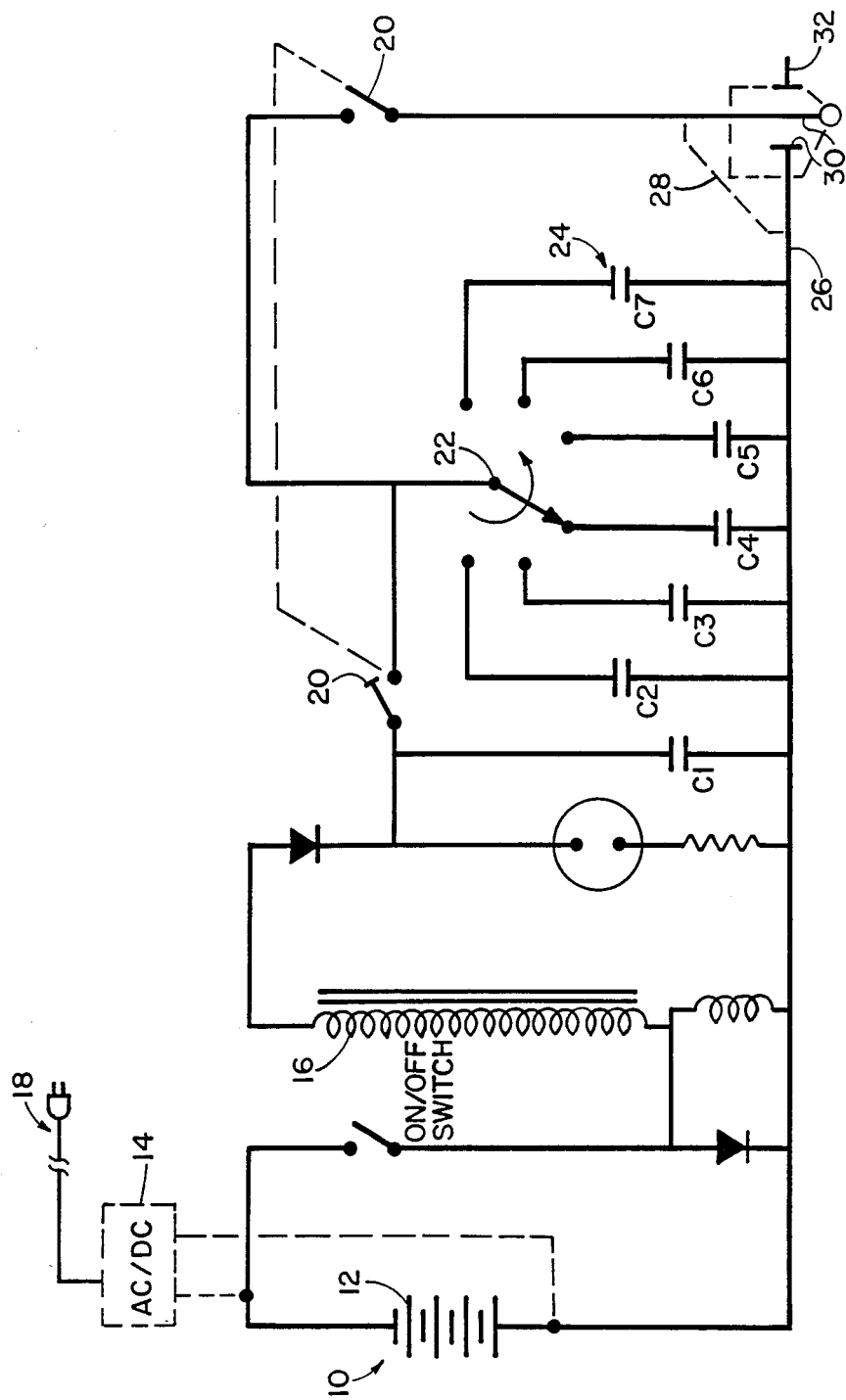

ELECTRICAL IMPULSE APPARATUS

BACKGROUND OF THE INVENTION

1. Field of the Invention

The present invention relates to medical/therapeutic devices and, more particularly, to such devices which apply electrical energy to living tissue.

2. Setting of the Invention

The application of electrical energy to living tissue for medical/therapeutic means is well known, such as described in U.S. Pat. No. 2,327,874; U.S. Pat. No. 2,507,572 and U.S. Pat. No. 4,667,677. In these patents various devices are described for generating a relatively mild current for treatment of affected tissue. However, there is no disclosure or suggestion in any of these patents of applying varying quantities of high voltage DC current to living tissue for reducing the adverse affects on living tissue of pest attacks and poison injection.

Various types of shock devices are currently marketed whereby a hand portable device includes a dry cell, a step-up transformer and a capacitor connected to a stationary or projectable set of electrodes. These devices are commonly referred to as "cattle prods" or "stun guns" respectively. While these devices do apply high voltage DC current to living tissue, the current is used to jolt or incapacitate a victim. There is no disclosure or suggestion of varying the voltage/amperage of these types of devices for medical/ therapeutic purposes.

A number of years ago the therapeutic affects of high voltage/ amperage applied to poison injection, such as from viper-type snakes, was discovered. In the June 1987 issue of *Outdoor Life* magazine, an article describes how various people and animals have been treated successfully by the application of high voltage direct current (DC) to the site of a snake bite. However, there is no disclosure or suggestion in this article of any device which can apply varying levels of electrical energy so that bites from poisonous snakes to insects can be treated by the same device.

There is a need for a device which can treat the adverse affects on living tissue from pest attacks and poison injection by the application of varying levels of high voltage direct current (DC).

SUMMARY OF THE INVENTION

The present invention has been disclosed to overcome the foregoing deficiencies and meet the above described needs. The present invention is a field portable electrical impulse apparatus useful for reducing the adverse affects on living tissue of pest attacks and poison injection. The apparatus includes a portable housing containing a source of direct current (DC) electrical energy. The voltage output can be increased to provide a high voltage source of direct current (DC) which is connected to a plurality of capacitors. The output of each capacitor can be selectively connected to a handheld probe, which is brought into contact with the living tissue. By being able to select the desired level of electrical power output from the probe, the operator can best choose what type of treatment is needed for the particular affected tissue.

BRIEF DESCRIPTION OF THE DRAWING

FIG. 1 is a semi-diagramatic view of the electrical circuitry of a medical/therapeutic device, made in accordance with one embodiment of the present invention.

DETAILED DESCRIPTION OF THE PREFERRED EMBODIMENTS

As shown in the FIG. 1, a source of direct current (DC) labled as reference numeral 10, is used with the apparatus of the present invention, and can be one or more dry or wet cell batteries 12. A suitable rectified connector device can be used to connect the apparatus to a household supply of alternating current (AC), such as 117 volts, 60 cycle. A fused transformer 16 is connected to the source of direct current and acts as a "step-up" transformer to increase the inPut voltage. If an alternating current (AC) is utilized, then a rectifier circuitry 18 of the type shown in FIG. 1 can be used as the suitable rectified connector device 14.

The electrical current from the source of direct current 10 is passed through a double pole, double throw (DP DT) switch 20, which permits the device to be in a charging or an armed/ready state. A contact of the switch 20 is connected to a voltage output device 22, such as a rotary multi-contact switch. Each contact of the device 22 is in turn connected to a capacitor 24, labled C2-C7, which have different ratings. Such capacitors can have ratings from about 0.20MFD/500V to about 17MFD/500V.

Each capacitor 24 is in turn connected to a lead 26, which can be removable by way of a plug/jack connector 28, to a hand held probe 30. The probe 30 includes a first electrode connected to the output of the capacitors 24 and a second electrode connected by way of a momentary switch 32 to the normally closed contacts of the switch 20. The electrodes and the probe 30 are sized and configured so that the outwardly extending electrodes can be brought into contact with the affected tissue.

The entire apparatus of the present invention can be housed in a relatively small, hand portable insulated case with the probe detachable (as shown in FIG. 1) or with the probe made as part of the insulated case. The source of direct current can be internal to the insulated case, or it can be separate for placement apart from the probe to reduce the weight to be carried by the hand holding the probe.

In using the present invention, the source of direct current is activated so that a charge will be built up on the selected capacitor 24. The switch 20 is tripped into a ready or armed state, whereupon the operator selects the desired output level to the probe by rotating the switch 22. The electrodes on the probe are placed against the affected tissue and the switch 32 is depressed, whereupon a jolt of electrical current in the form of high voltage direct current (DC) is applied to the affected tissue. The switch 20 is tripped to start the charging process again and the procedure can be repeated as desired.

An important feature of the present invention is that different levels of electrical energy can be utilized so everything from a chigger bite to a snake bite can be effectively treated. For example, for chigger bites, bee stings and mosquito bites, a charge of from about 350 volts DC, 0.05 amperies to about 350 volts DC, 0.1 amperies has proven effective. For in-place ticks, a relatively low charge of about 350 volts DC, 0.2 amperies can be applied to the tick to cause it to release from the living tissue. Too high of an initial voltage will kill the tick which will not leave its head within the living tissue. After the tick has backed away from the living tissue, a charge of about 350 volts DC, 0.2 amperies can be applied to the bite site to nullify any injected fluids. For a venomous snake bite, about 4-6 applicatons of about 20,000 volts DC, 10 A/1 Mili. Sec. Time has been found to be effective. At higher voltage levels, it has been found best to delay the application of repeated shocks for about 2 minutes between applications.

Whereas the present invention has been described in particular relation to the above identified drawing, it should be understood that other and further modifications, apart from those shown or suggested herein, maybe made within the scope and spirit 15 of the present invention.

What is claimed is:

1. A field portable electrical impulse apparatus useful for reducing the adverse affects on living tissue of pest attacks and poison injection, comprising:

housing containing a source of direct current (DC) electrical energy;

means within the housing for increasing the voltage output from the source of direct current (DC) electrical energy, the increased voltage means including a grounded contact and an output contact;

a plurality of capacitors each having a different amperage output, each capacitor being in operative contact with the grounded contact;

a selection means being in operative contact with the output contact of one of said capacitors at one time; and probe adapted for contact with living tissue comprising a first exposed electrode being in operative contact to the grounded contact, and a second exposed electrode being in operative contact by way of a momentary switch with an output of the selection means.

whereby different levels of current can be applied via the probe to living tissue to reduce the adverse affects on living tissue of pest attacks and poison injection.

2. The apparatus of claim 1 whereby the source of direct current (DC) electrical energy comprises one or more dry cell batteries.

3. The apparatus of claim 1 whereby the source of direct current (DC) electrical energy comprises a rectifier connectable to a source of alternating current.

4. The appartus of claim 1 whereby the rating from the of capacitors is from about 0.20 MFD to about 17 MFD/500 V.

* * * * *